US010542933B2

(12) United States Patent
Sato et al.

(10) Patent No.: US 10,542,933 B2
(45) Date of Patent: Jan. 28, 2020

(54) EXERCISE TEST EVALUATION SYSTEM, EXERCISE TEST EVALUATION APPARATUS, EXERCISE TEST EVALUATION METHOD, AND NON-TRANSITORY COMPUTER READABLE RECORDING MEDIUM

(71) Applicant: Panasonic Intellectual Property Management Co., Ltd., Osaka (JP)

(72) Inventors: Yoshikuni Sato, Osaka (JP); Toru Nakada, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 175 days.

(21) Appl. No.: 15/666,864

(22) Filed: Aug. 2, 2017

(65) Prior Publication Data
US 2018/0055446 A1 Mar. 1, 2018

(30) Foreign Application Priority Data

Aug. 23, 2016 (JP) .................................. 2016-162349
Aug. 23, 2016 (JP) .................................. 2016-162350
Mar. 31, 2017 (JP) .................................. 2017-070691

(51) Int. Cl.
*A61B 5/00* (2006.01)
*A61B 5/0205* (2006.01)
(Continued)

(52) U.S. Cl.
CPC .......... *A61B 5/4866* (2013.01); *A61B 5/0205* (2013.01); *A61B 5/02438* (2013.01);
(Continued)

(58) Field of Classification Search
CPC .......... A61B 5/01; A61B 5/02; A61B 5/0205; A61B 5/02438; A61B 5/861; A61B 5/112; A61B 5/1118; A61B 5/7221
See application file for complete search history.

(56) References Cited

U.S. PATENT DOCUMENTS

2014/0088444 A1* 3/2014 Saalasti ................ A61B 5/0205
                                                    600/484
2016/0000373 A1* 1/2016 Karavirta ............ G06F 19/3481
                                                    702/19
(Continued)

FOREIGN PATENT DOCUMENTS

WO           1997/037588           10/1997

OTHER PUBLICATIONS

Gordon H. Guyatt et al., "The 6-minute walk: a new measure of exercise capacity in patients with chronic heart failure", Canadian Medical Association Journal, vol. 132(8), pp. 919-923, Apr. 1985.

*Primary Examiner* — Michael W Kahelin
*Assistant Examiner* — Sana Sahand
(74) *Attorney, Agent, or Firm* — Wenderoth, Lind & Ponack, L.L.P.

(57) ABSTRACT

An exercise test evaluation system includes an acceleration sensor that is worn by a user during an exercise test and acquires acceleration values of a foot of the user, a heart rate sensor that is worn by the user and measures a heart rate of the user, and a processor. The processor acquires a first maximum acceleration value and a second maximum acceleration value, calculates a reliability score using the first and second maximum acceleration values, acquires a walking velocity and a heart rate of the user and estimates a maximum oxygen intake amount using the user's walking velocity and heart rate if the reliability score is equal to or higher than a specific threshold value, and estimates the maximum
(Continued)

oxygen intake amount using the user's walking velocity if the reliability score is lower than the specific threshold value.

7 Claims, 8 Drawing Sheets

(51) Int. Cl.
  *A61B 5/024* (2006.01)
  *A61B 5/11* (2006.01)
(52) U.S. Cl.
  CPC ............ *A61B 5/1114* (2013.01); *A61B 5/1118* (2013.01); *A61B 5/7221* (2013.01); *A61B 5/7278* (2013.01); *A61B 5/112* (2013.01); *A61B 2503/10* (2013.01); *A61B 2562/0219* (2013.01)

(56) References Cited

U.S. PATENT DOCUMENTS

| | | | |
|---|---|---|---|
| 2016/0143579 A1* | 5/2016 | Martikka | A61B 5/486 600/301 |
| 2017/0056725 A1* | 3/2017 | Nakada | A61B 5/0205 |
| 2017/0202486 A1* | 7/2017 | Martikka | A61B 5/1118 |
| 2017/0360368 A1* | 12/2017 | Aoshima | A63B 24/0062 |
| 2018/0192935 A1* | 7/2018 | Jang | G06F 19/00 |
| 2018/0249917 A1* | 9/2018 | Sasahara | A61B 5/1118 |

\* cited by examiner

FIG. 5

| TIME SEQUENCE NUMBER | TIME SEGMENT | MAXIMUM ACCELERATION (mG) |
|---|---|---|
| 1 | 0 - 1 MINUTES | 26000 |
| 2 | 1 - 2 MINUTES | 26400 |
| 3 | 2 - 3 MINUTES | 24800 |
| 4 | 3 - 4 MINUTES | 24500 |
| 5 | 4 - 5 MINUTES | 22700 |
| 6 | 5 - 6 MINUTES | 23000 |

EXERCISE TEST EVALUATION SYSTEM, EXERCISE TEST EVALUATION APPARATUS, EXERCISE TEST EVALUATION METHOD, AND NON-TRANSITORY COMPUTER READABLE RECORDING MEDIUM

BACKGROUND

1. Technical Field

The present disclosure relates to an exercise test evaluation system, an exercise test evaluation apparatus, an exercise test evaluation method, and a non-transitory computer readable recording medium for evaluating the reliability of an exercise test.

2. Description of the Related Art

Information concerning exercise capacity including walking function is important when contents of a rehabilitation plan of a person are determined. The persons' falls caused by sarcopenia or a decreased walking function have recently become a problem in society, and there is an increasing demand on easily and accurately evaluating the walking function of persons. Walking abilities of persons include muscular strength, endurance, and physical balance ability. The paper written by Guyatt G H et al. entitled "The 6-minute walk: a new measure of exercise capacity in patients with chronic heart failure", Canadian Medical Association Journal, 132(8): 919-923, 1985, discloses a 6-minute walk test that evaluates physical endurance. The 6-minute walk test uses an index of physical endurance of a travel distance of 6 minutes, and is in widespread use in clinical medicine field. Since physical endurance significantly depends on cardiopulmonary functions, information related to a heart rate is used in addition to the travel distance. The technique disclosed in Japanese Patent No. 3608204 is a technique of estimating a maximum oxygen intake amount, as one of accurate indexes of physical endurance, from an exercise load and heart rate, which are measured using a wristband type portable terminal during running. The exercise load is determined from a value that results from multiplying a subject's weight by a running velocity.

The technique disclosed in the paper by Guyatt G H et al. evaluates physical endurance with a low exercise load, but reliability of the evaluation results is subject to variations because a larger difference in travel distance is caused depending on the degree of subjects' efforts. The technique disclosed in Japanese Patent 3608204 is based on a steady state during running, and the degree of subjects' efforts affects estimation accuracy as in the technique disclosed by the paper by Guyatt G H et al.

SUMMARY

One non-limiting and exemplary embodiment provides an exercise test evaluation system, an exercise test evaluation apparatus, an exercise test evaluation method, and a non-transitory computer readable recording medium for improving an estimation accuracy of exercise capacity of a subject from an exercise test.

In one general aspect, the techniques disclosed here feature an exercise test evaluation system. The exercise test evaluation system include an acceleration sensor that is worn by a user having an exercise test and acquires acceleration values of a foot of the user, a heart rate sensor that is worn by the user having the exercise test and measures a heart rate of the user, a processor; and an outputter. The processor acquires a first maximum acceleration value within a first time period and a second maximum acceleration value within a second time period after the first time period in response to the acceleration values. The processor calculates a reliability score of the exercise test using the first maximum acceleration value and the second maximum acceleration value. If the reliability score is equal to or higher than a specific threshold value, the processor acquires a walking velocity and a heart rate of the user during the exercise test, and estimates a maximum oxygen intake amount using the user's walking velocity and heart rate. If the reliability score is lower than the specific threshold value, the processor acquires the user's walking velocity, and estimates the maximum oxygen intake amount using the user's walking velocity. The outputter outputs the maximum oxygen intake amount.

In accordance with the disclosure, the estimation accuracy in estimating the exercise capacity of the subject from the exercise test is increased.

It should be noted that general or specific embodiments may be implemented as a system, a method, an integrated circuit, a computer program, a non-transitory computer readable recording medium, or any selective combination thereof. The non-transitory computer readable recording medium may include a non-volatile recording medium, such as a compact disk read-only memory (CD-ROM).

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 5 illustrates an example of data to be stored on a memory of FIG. 1;

DETAILED DESCRIPTION

Figure 1:
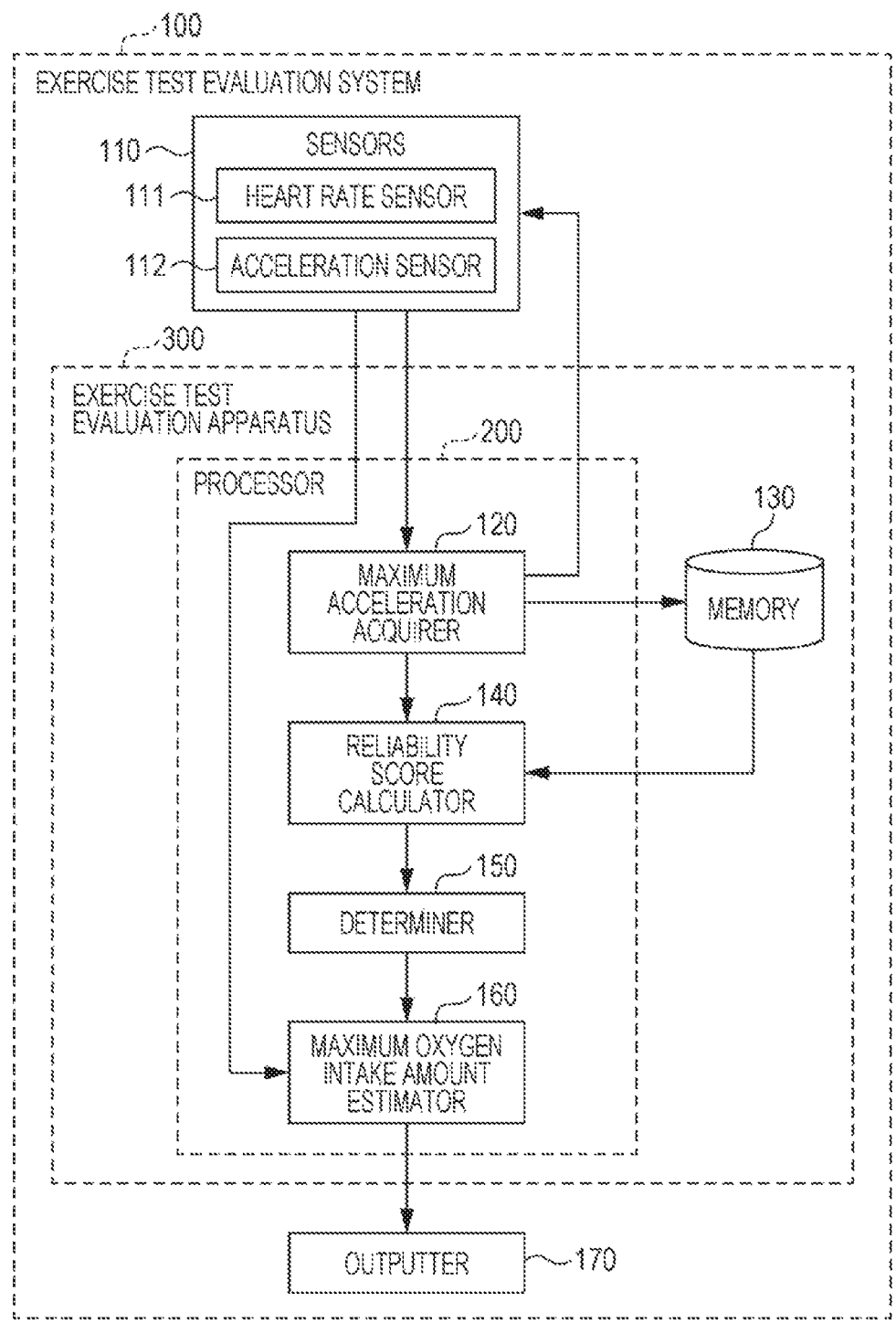
FIG. 1 is a block diagram illustrating an exercise test evaluation system of a first embodiment.

Inventors of the disclosure have studied the techniques disclosed in the paper by Guyatt G H et al. and Japanese Patent No. 3608204 described in "Background of the Related Art" and have found that the results related to the exercise capacity of the subject from these techniques are significantly influenced by the degree of the subject's efforts during the exercise test. The inventors have reached the conclusion that the estimation accuracy of the exercise capacity of the subject is low in the techniques disclosed in the paper by Guyatt G H et al. and Japanese Patent No. 3608204. The inventors have studied the technique of estimating the exercise capacity of the subject from the measurement results in the exercise test, and have developed a technique described below to increase the estimation accuracy.

According to an aspect of the disclosure, there is provided an exercise test evaluation system. The exercise test evaluation system includes an acceleration sensor that is worn by a user having an exercise test and acquires acceleration values of a foot of the user, a heart rate sensor that is worn by the user having the exercise test and measures a heart rate of the user, a processor, and an outputter. The processor acquires a first maximum acceleration value within a first time period and a second maximum acceleration value within a second time period after the first time period in response to the acceleration values, calculates a reliability score of the exercise test using the first maximum acceleration value and the second maximum acceleration value, acquires a walking velocity and a heart rate of the user during the exercise test and estimates a maximum oxygen intake amount using the user's walking velocity and heart rate if the reliability score is equal to or higher than a specific threshold value, and acquires the user's walking velocity and estimates the maximum oxygen intake amount using the user's walking velocity if the reliability score is lower than the specific threshold value. The outputter outputs the maximum oxygen intake amount.

According to the aspect, the reliability score may be related to the relationship between the first maximum acceleration value and the second maximum acceleration value within the two time periods. For example, the relationship between the first maximum acceleration value and the second maximum acceleration value changes from a higher-reliability exercise test in which a user may make an exercise effort to a lower-reliability exercise test in which a user may not bother to make a sufficient effort. The reliability score thus changes accordingly. The reliability score may numerically indicate the reliability of the exercise test. The degree of the users effort and the users heart rate may affect each other during the exercise test. For this reason, an estimation method of the maximum oxygen intake amount may change in response to the value of the reliability score. More specifically, if the reliability score is lower, for example, lower than a first specific threshold value, the estimation accuracy of the maximum oxygen intake amount that has been estimated without using the user's heart rate is increased. If the reliability score is higher, for example, equal to or higher than the first specific threshold value, the estimation accuracy of the maximum oxygen intake amount that has been estimated using two factors, including the user's walking velocity and heart rate, is increased. In this way, the estimation accuracy of the exercise capacity of the subject having undergone the exercise test is thus increased.

In the exercise test evaluation system of another aspect of the disclosure, the acceleration sensor may acquire the acceleration values during specific time periods. The specific time periods include a plurality of time-sequenced time periods including the first time period, and the second time period. From among the maximum acceleration values of the time periods, one of the first maximum acceleration value and the second maximum acceleration value is minimum, and the other of the first maximum acceleration value and the second maximum acceleration value is maximum. The processor calculates as the reliability score a difference between a time sequence number of the first time period having the first maximum acceleration value and a time sequence number of the second time period having the second maximum acceleration value.

In accordance with the embodiment, the maximum acceleration values within the time periods remain almost constant or are decreasing with time if the user is making an exercise effort during the exercise test. If the reliability score is zero or positive, it is recognized that the user is making an exercise effort during the exercise test, and that the results of the exercise test are reliable. On the other hand, if the reliability score is negative, the user may not bother to make an exercise effort during the exercise test and the results of the exercise test may not be reliable. The reliability score is used to indicate the reliability of the exercise test in a simple fashion.

In the exercise test evaluation system of another aspect of the disclosure, the acceleration sensor may acquire the acceleration values during specific time periods. The specific time periods includes the first time period, a third time period, and the second time period in that time order. The processor may acquire a third maximum acceleration value within the third time period, acquire each of differences respectively between sequential order numbers according to which the first maximum acceleration value, the second maximum acceleration value, and the third maximum acceleration value are arranged in an order of from larger to smaller magnitude and time sequence numbers of sequential time order according to which the time periods respectively corresponding to the first maximum acceleration value, the second maximum acceleration value, and the third maximum acceleration value are arranged, and calculate a sum of absolute values of the differences as the reliability score.

According to the aspect of the disclosure, the absolute values acquired during the time periods are the absolute values of the differences respectively between the sequential order numbers of the maximum acceleration values within all the time periods and the time sequence numbers of all the time periods. The maximum acceleration values within the time periods remain almost constant or are decreasing with time if the user is making an exercise effort during the exercise test. The absolute value is thus lower. On the other hand, if the user does not bother to make an exercise effort during the exercise test, the absolute value is higher. For this reason, as the sum of the absolute values is larger, the reliability of the exercise test is decreased. The reliability score serves as the reliability of the exercise test in a simple way.

In the exercise test evaluation system of another aspect of the disclosure, the processor may acquire a gait cycle of the user in response to the acceleration values, and acquire the first time period and the second time period in response to the gait cycle. According to the aspect, the maximum acceleration value within each time period acquired in response to the gait cycle indicates the user's walking status and a change in the user's walking status more in detail and more accurately. The accuracy of the reliability score is thus increased.

According to another aspect of the disclosure, there is provided an exercise test evaluation apparatus. The exercise test evaluation apparatus includes a processor. The processor may acquire acceleration values of a foot of a user during an exercise test, acquire a heart rate of the user, acquire a first maximum acceleration value within a first time period and a second maximum acceleration value within a second time period after the first time period in response to the acceleration values, calculate a reliability score of the exercise test using the first maximum acceleration value and the second maximum acceleration value, acquire a walking velocity and a heart rate of the user during the exercise test and estimate a maximum oxygen intake amount using the user's walking velocity and heart rate if the reliability score is equal to or higher than a specific threshold value, acquire the user's walking velocity and estimate the maximum oxygen intake amount using the user's walking velocity if the reliability score is lower than the specific threshold value, and outputs the maximum oxygen intake amount. According the aspect of the disclosure, an effect similar to the effect of the exercise test evaluation system described above is provided.

According another aspect of the disclosure, there is provided a non-transitory computer readable recording medium. The non-transitory computer readable recording medium is non-volatile and stores a control program causing an apparatus including a processor to perform a process. The process includes acquiring acceleration values of a foot of a user during an exercise test, acquiring a heart rate of the user, acquiring a first maximum acceleration value within a first time period, and a second maximum acceleration value within a second time period after the first time period in response to the acceleration values, calculating a reliability score of the exercise test using the first maximum acceleration value and the second maximum acceleration value, acquiring a walking velocity and a heart rate of the user during the exercise test and estimating a maximum oxygen intake amount using the user's walking velocity and heart rate if the reliability score is equal to or higher than a specific threshold value, acquiring the user's walking velocity and estimating the maximum oxygen intake amount using the user's walking velocity if the reliability score is lower than the specific threshold value, and outputting the maximum oxygen intake amount. According to the aspect, an effect similar to the effect of the exercise test evaluation system is provided.

In the non-transitory computer readable recording medium of another aspect of the disclosure, the process may further include acquiring the acceleration values during specific time periods, the specific time periods including a plurality of time-sequenced time periods including the first time period, and the second time period, one of the first maximum acceleration value and the second maximum acceleration value being minimum, and the other of the first maximum acceleration value and the second maximum acceleration value being maximum from among the maximum acceleration values of the time periods, and calculating as the reliability score a difference between a time sequence number of the first time period having the first maximum acceleration value and a time sequence number of the second time period having the second maximum acceleration value.

In the non-transitory computer readable recording medium of another aspect of the disclosure, the process may further include acquiring the acceleration values during specific time periods, the specific time periods including the first time period, a third time period, and the second time period in time order, acquiring a third maximum acceleration value within the third time period in response to the acceleration values, acquiring each of differences respectively between sequential order numbers according to which the first maximum acceleration value, the second maximum acceleration value, and the third maximum acceleration value are arranged in order of from larger to smaller magnitude and time sequence numbers of sequential time order according to which the time periods respectively corresponding to the first maximum acceleration value, the second maximum acceleration value, and the third maximum acceleration value are arranged, and calculating a sum of absolute values of the differences as the reliability score.

In the non-transitory computer readable recording medium of another aspect of the disclosure, the process may further include acquiring a gait cycle of the user in response to the acceleration values, and acquiring the first time period and the second time period in response to the gait cycle.

According to another aspect of the disclosure, there is provided an exercise test evaluation method. The exercise test evaluation method includes acquiring acceleration values of a foot of a user during an exercise test, acquiring a heart rate of the user, acquiring a first maximum acceleration value within a first time period and a second maximum acceleration value within a second time period after the first time period in response to the acceleration values, calculating a reliability score of the exercise test using the first maximum acceleration value and the second maximum acceleration value, acquiring a walking velocity and a heart rate of the user during the exercise test and estimating a maximum oxygen intake amount using the user's walking velocity and heart rate if the reliability score is equal to or higher than a specific threshold value, acquiring the user's walking velocity and estimating the maximum oxygen intake amount using the user's walking velocity if the reliability score is lower than the specific threshold value, and outputting the maximum oxygen intake amount. According to the aspect of the disclosure, an effect similar to the effect of the exercise test evaluation system is provided.

According to another aspect of the disclosure, there is provided an exercise test evaluation system. The exercise test evaluation system includes an acceleration sensor that is worn by a user during an exercise test and acquires acceleration values of a foot of the user, a processor, and an outputter. The processor acquires a first maximum acceleration value within a first time period and a second maximum acceleration value within a second time period after the first time period in response to the acceleration values, calculates a reliability score of the exercise test using the first maximum acceleration value and the second maximum acceleration value. The outputter outputs the reliability score.

According to the above-described aspect, the reliability score may be related to the relationship between the first maximum acceleration value and the second maximum acceleration value within the two time periods. For example, the relationship between the first maximum acceleration value and the second maximum acceleration value changes from a higher-reliability exercise test in which a user may make an exercise effort to a lower-reliability exercise test in which a user may not bother to make a sufficient effort. The reliability score thus changes accordingly. The reliability score may numerically indicate the reliability of the exercise test. For example, the user of the exercise test evaluation system may determine the reliability of the results of the exercise test, based on the reliability score. Alternatively, the exercise test evaluation system may determine the reliability, based the reliability score. More specifically, based on the determination results, the exercise test evaluation system may display an error message in the results of the exercise test or recommend that the user perform the exercise test again. The exercise test evaluation system may increase the estimation accuracy of the exercise capacity of the user using the information of the user using the user's foot acceleration during the exercise test.

In the exercise test evaluation system of another aspect of the disclosure, the acceleration sensor acquires the acceleration values during specific time periods. The specific time periods include a plurality of time-sequenced time periods including the first time period, and the second time period. From among the maximum acceleration values of the time periods, one of the first maximum acceleration value and the second maximum acceleration value is minimum, and the other of the first maximum acceleration value and the second maximum acceleration value is maximum. The processor calculates as the reliability score a difference between a time sequence number of the first time period having the first maximum acceleration value and a time sequence number of the second time period having the second maximum acceleration value.

In accordance with the aspect described above, the maximum acceleration values within the time periods remain almost constant or are decreasing with time if the user is making an exercise effort during the exercise test. If the reliability score is zero or positive, it is recognized that the user is making an exercise effort during the exercise test, and that the results of the exercise test are reliable. On the other hand, if the reliability score is negative, the user may not bother to make an exercise effort during the exercise test and the results of the exercise test may not be reliable. The reliability score is used to indicate the reliability of the exercise test in a simple way.

In the exercise test evaluation system of another aspect of the disclosure, the acceleration sensor may acquire the acceleration values during specific time periods. The specific time periods may include the first time period, a third time period, and the second time period in that time order. The processor may acquire a third maximum acceleration value within the third time period, acquire each of differences respectively between sequential order numbers according to which the first maximum acceleration value, the second maximum acceleration value, and the third maximum acceleration value are arranged in an order of from larger to smaller magnitude and time sequence numbers of sequential time order according to which the time periods respectively corresponding to the first maximum acceleration value, the second maximum acceleration value, and the third maximum acceleration value are arranged, and calculate a sum of absolute values of the differences as the reliability score.

According to the aspect of the disclosure, the absolute values acquired during the time periods are the absolute values of the differences respectively between the sequential order numbers of the maximum acceleration values within all the time periods and the time sequence numbers of all the time periods. The maximum acceleration values within the time periods remain almost constant or are decreasing with time if the user is making an exercise effort during the exercise test. The absolute value is thus lower. On the other hand, if the user does not bother to make an exercise effort during the exercise test, the absolute value is higher. For this reason, as the sum of the absolute values is larger, the reliability of the exercise test is decreased. The reliability score serves as the reliability of the exercise test in a simple way.

In the exercise test evaluation system of another aspect of the disclosure, the processor may acquire a gait cycle of the user in response to the acceleration values, and acquire the first time period and the second time period in response to the gait cycle. According to the aspect, the maximum acceleration value within each time period acquired in response to the gait cycle indicates the user's walking status and a change in the user's walking status more in detail and more accurately. The accuracy of the reliability score is thus increased.

According to another aspect of the disclosure, there is provided an exercise test evaluation apparatus. The exercise test evaluation apparatus includes a processor. The processor acquires acceleration values of a foot of a user during an exercise test, acquires a first maximum acceleration value within a first time period and a second maximum acceleration value within a second time period after the first time period in response to the acceleration values, calculates a reliability score of the exercise test using the first maximum acceleration value and the second maximum acceleration value, and outputs the reliability score. According to the aspect of the disclosure, the exercise test evaluation apparatus provides an effect similar to the effect of the exercise test evaluation system of the aspect described above.

According another aspect of the disclosure, there is provided a computer program that causes a computer to perform a process. The process includes acquiring acceleration values of a foot of a user during an exercise test, acquiring a first maximum acceleration value within a first time period and a second maximum acceleration value within a second time period after the first time period in response to the acceleration values, calculating a reliability score of the exercise test using the first maximum acceleration value and the second maximum acceleration value, and outputs the reliability score. According to the aspect of the disclosure, the exercise test evaluation apparatus provides an effect similar to the effect of the exercise test evaluation system of the aspect described above.

In the computer program of another aspect of the disclosure, the process may further include acquiring the acceleration values during specific time periods, the specific time periods including a plurality of time-sequenced time periods including the first time period, and the second time period, one of the first maximum acceleration value and the second maximum acceleration value being minimum, and the other of the first maximum acceleration value and the second maximum acceleration value being maximum from among the maximum acceleration values of the time periods, and calculating as the reliability score a difference between a time sequence number of the first time period having the first maximum acceleration value and a time sequence number of the second time period having the second maximum acceleration value.

In the computer program of another aspect of the disclosure, the process may further include acquiring the acceleration values during specific time periods, the specific time periods including the first time period, a third time period, and the second time period in that time order, acquiring a third maximum acceleration value within the third time period in response to the acceleration values, acquiring each of differences respectively between sequential order numbers according to which the first maximum acceleration value, the second maximum acceleration value, and the third maximum acceleration value are arranged in order of from larger to smaller magnitude and time sequence numbers of sequential time order according to which the time periods respectively corresponding to the first maximum acceleration value, the second maximum acceleration value, and the third maximum acceleration value are arranged, and calculating a sum of absolute values of the differences as the reliability score.

In the computer program of another aspect of the disclosure, the process may further include acquiring a gait cycle of the user in response to the acceleration values, and acquiring the first time period and the second time period in response to the gait cycle.

According to another aspect of the disclosure, there is provided an exercise test evaluation method. The exercise test evaluation method includes acquiring acceleration values of a foot of a user during an exercise test, acquiring a first maximum acceleration value within a first time period and a second maximum acceleration value within a second time period after the first time period in response to the acceleration values, calculating a reliability score of the exercise test using the first maximum acceleration value and the second maximum acceleration value, and outputting the reliability score. According to the aspect of the disclosure, the exercise test evaluation method provides an effect similar to the effect of the exercise test evaluation system of the aspect described above.

The general or specific embodiments may be implemented as a system, a method, an integrated circuit, a computer program, a non-transitory computer readable recording medium, or any selective combination thereof. The non-transitory computer readable recording medium may include a non-volatile recording medium, such as a compact disk read-only memory (CD-ROM).

The exercise test evaluation systems as embodiments are described with reference to the drawings. Each of the embodiments described below represents a general or specific example of the disclosure. Numerical values, shapes, materials, elements, layout locations of the elements, an interconnection form, steps and the order of the steps in the embodiments are described for exemplary purposes only, and are not intended to limit the disclosure. Elements not described in independent claims indicative of a generic concept, from among the elements of the embodiments, may be any elements. In the discussion that follows, phrases including the word "approximately", such as approximately parallel or approximately perpendicular, may be used. The phrase "approximately parallel" is intended to mean not only "completely parallel" but also "substantially parallel". For example, a "substantially parallel" state is still considered to hold even if a deviation of several percent occurs from a completely parallel state. The same is true of phrases that include the word "approximately".

First Embodiment 1.1 Configuration of Exercise Test Evaluation System of First Embodiment Referring to FIG. 1, an exercise test evaluation system 100 of a first embodiment is described. FIG. 1 is a block diagram illustrating the exercise test evaluation system 100 of the first embodiment. The exercise test evaluation system 100 estimates the status of the exercise capacity of a subject from measurement results from the exercise test of the subject. More specifically, the exercise test evaluation system 100 of the first embodiment estimates a maximum oxygen intake amount of the subject. In view of this, the exercise test evaluation system 100 of the first embodiment is also referred to as a maximum oxygen intake amount estimating system. In the discussion that follows, the subject also referred to as a user.

The exercise test of the first embodiment means measurement that is performed to detect the status of the user in the exercise capacity. An example of the user's status is a walking ability to move. An example of the exercise test related to walking is a 6-minute walk test (6MWT). The 6-minute walk test is a load test of walking at a constant velocity. More specifically, a subject walks as fast as he or she can for a period of 6 minutes, and exercise tolerance of the subject is evaluated in accordance with a travel distance achieved in the test.

For the 6-minute walk test, reference is made to American Thoracic Society (ATS) statement: guidelines for the six-minute walk test, American Journal of Respiratory and Critical Care Medicine (Am J Respir Crit Care Med), 166: 111-117, 2002.

Another example of the exercise test for walking is a shuttle walking test In the shuttle waling test, the subject walks along a 10 meter course in synchronization with a signal sound and is evaluated in terms of a maximum exercise capacity. The exercise test is not limited to walking. For example, the exercise test may be a running test of the subject who runs a specific distance.

Referring to FIG. 1, the exercise test evaluation system 100 includes sensors 110, an exercise test evaluation apparatus 300, and an outputter 170. The exercise test evaluation apparatus 300 is also referred to as a maximum oxygen intake amount estimating apparatus. The exercise test evaluation apparatus 300 includes a processor 200 and a memory 130. The exercise test evaluation system 100 may include a single apparatus or multiple apparatuses. Part or whole of the exercise test evaluation system 100 may be built in another apparatus, and may thus form part of the apparatus.

Sensors

Figure 2:
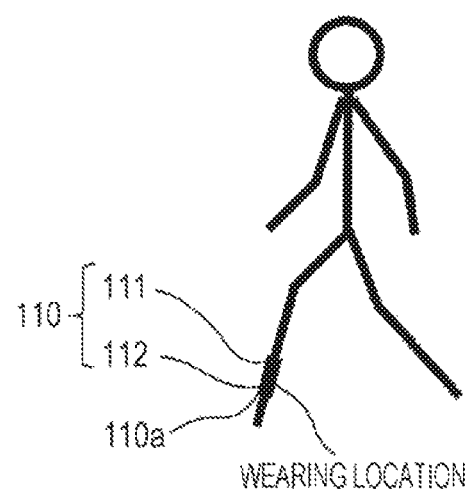
FIG. 2 illustrates a wearing example of a sensor of FIG. 1 to a subject.

The sensors 110 include a heart rate sensor 111 and an acceleration sensor 112. The heart rate sensor 111 measures a heart rate of the user. As illustrated in FIG. 2, the heart rate sensor 111 is worn on a wrist, an ankle, or the chest of the user, for example. FIG. 2 illustrates a wearing example of the sensors 110 of FIG. 1 to the user. The heart rate sensor 111 outputs measurement results to the processor 200.

The acceleration sensor 112 is mounted on part of the user's body serving as a measurement target, and measures an acceleration of the measurement target. The acceleration sensor 112 outputs the measurement results to the processor 200. In accordance with the first embodiment, the acceleration sensor 112 is a one-axis acceleration sensor that measures acceleration in one axis. Alternatively, the acceleration sensor 112 may be a two-axis acceleration sensor that measures acceleration in two mutually perpendicular directions, or a three-axis acceleration sensor that measures acceleration in three mutually perpendicular directions. The acceleration sensor working in two or more axes may detect acceleration in a desired direction regardless of the mounting location of the acceleration sensor.

In accordance with the first embodiment, the mounting location of the acceleration sensor 112 is not limited to any particular part of the body of the user, but the acceleration sensor 112 is typically worn around a leg of the user to measure acceleration of the foot of the user in the moving direction of the user. For example, the acceleration sensor 112 measures acceleration of the foot of the user during an exercise test. The exercise test may include walking or running. The moving direction of the user is the same direction in which the user is walking or running. The acceleration sensor 112 is worn on a foot of the user during the exercise test. More specifically, the acceleration sensor 112 is worn at a location on or close to an ankle of the user. The location close to the ankle of the user may include the ankle, the instep of the foot, and the sole of the foot. As illustrated in FIG. 2, the acceleration sensor 112 may be worn around at least one ankle of the user. For example, the acceleration sensor 112 is mounted on a band 110a that is wrapped around the ankle of the user. Alternatively, the acceleration sensor 112 may be mounted inside a shoe of the user.

Figure 3:
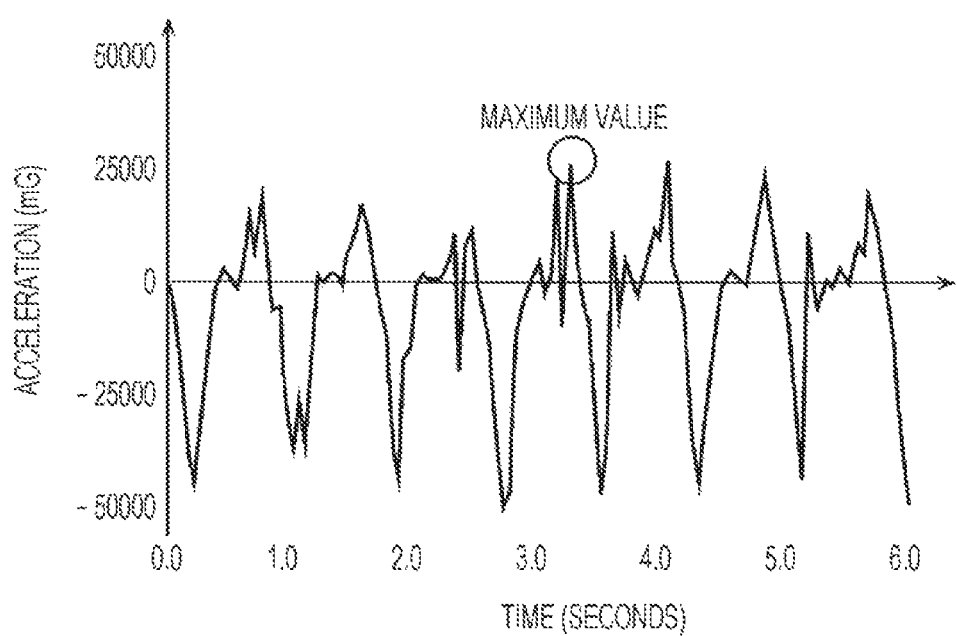
FIG. 3 illustrates an example of measurement results of the movement of an acceleration sensor in a direction of movement when a subject walks during an exercise test.

FIG. 3 is a graph that plots an example of measurement results of the acceleration sensor 112 in a direction of movement when the user is walking during an exercise. FIG. 3 illustrates an example of the measurement results of the acceleration sensor 112 when the user is walking in the moving direction during the exercise test. More specifically, FIG. 3 illustrates an example of the measurement results of the acceleration sensor 112 during a time segment of a 6-minute walk test that serves as one of the exercise tests. In other words, FIG. 3 illustrates measurement data of acceleration during a time period of 6 seconds. The vertical axis of FIG. 3 represents acceleration (mG), and the horizontal axis of FIG. 3 represents time (seconds). Note that 1 G=9.80665 m/s$^2$. In the graph of FIG. 3, acceleration in the moving direction of the user is a positive value.

Exercise Test Evaluation Apparatus

The exercise test evaluation apparatus 300 includes the processor 200 and the memory 130. The exercise test evaluation apparatus 300 may be hardware including these elements. The exercise test evaluation apparatus 300 may be a circuit, such as a computer, a micro processing unit (MPU), a central processing unit (CPU), a processor, or a large scale integration (LSI), or an integrated circuit card (IC card), or a unitary module. The exercise test evaluation apparatus 300 may be mounted together with the sensors 110 on the band 110a as illustrated in FIG. 2, and communicate with the outputter 170 or a device including the outputter 170 through wireless or wired communication. Alternatively, the exercise test evaluation apparatus 300 may be mounted at a remote location spaced away from the sensors 110 and communicate with the sensors 110 through wireless or wired communication. In this case, the exercise test evaluation apparatus 300 alone may form a single module, and may be built in another apparatus, such as a computer. The wired communication may be any type of currently available wired communication. The wireless communication may be any type of currently available wireless communication. For example, the wireless communication may be a wireless local area network (LAN), such as Wireless Fidelity (Wi-Fi (registered trademark)), or short-range wireless communication, such as Bluetooth (registered trademark), or ZigBee (registered trademark).

Processor

The processor 200 generally controls the exercise test evaluation apparatus 300. The processor 200 receives the measurement results from the sensors 110. The processor 200 stores on the memory 130 a variety of information including the measurement results acquired from the sensors 110, or reads a variety of information stored on the memory 130. The processor 200 also outputs information to the outputter 170. Based on an acceleration value from the sensors 110, the processor 200 calculates a reliability score of the exercise test.

The processor 200 includes a maximum acceleration acquirer 120, a reliability score calculator 140, a determiner 150, and a maximum oxygen intake amount estimator 160.

The processor 200 and other elements may be implemented as dedicated hardware, or may be implemented by executing a software program that corresponds to each of the elements. The processor 200 and the other elements may be implemented by the CPU or the processor when the CPU or the processor reads the software program stored on a recording medium, such as a hard disk, a semiconductor memory, or the like, and executes the read software program. The software program may be stored, in advance, on a recording medium as a product, such as a memory of the exercise test evaluation apparatus 300. The software program may be supplied in a recorded state on a recording medium as a product, such as a compact disk read-only memory (CD-ROM). The software program may be transmitted via a telecommunication network, such as the Internet, and acquired to be stored on a memory, or may be obtained via the recording medium and then stored on the memory as a computer memory.

The maximum acceleration acquirer 120 receives an acceleration value as the measurement results of acceleration from the acceleration sensor 112 of the sensors 110, and stores the acceleration value on the memory 130. The maximum acceleration acquirer 120 calculates and acquires a maximum acceleration value from among the acceleration values within a specific time period received from the acceleration sensor 112. Referring to FIG. 3, the specific time period is 6.0 seconds. The maximum acceleration acquirer 120 acquires as the maximum acceleration value an acceleration value of 25800 mG at a time point of 3.2 seconds from among the acceleration values detected within the specific time period of 6.0 seconds. The maximum acceleration acquirer 120 acquires the maximum acceleration values respectively from multiple specific time periods, thereby acquiring multiple maximum acceleration values. The maximum acceleration acquirer 120 may output the maximum acquired acceleration values to the reliability score calculator 140.

The reliability score calculator 140 acquires the multiple maximum acceleration values stored on the memory 130, and calculates a reliability score representing the reliability of the exercise test, based on the multiple maximum acceleration values acquired. The reliability score is an index as to whether the measurement results of the exercise test accurately indicate the status of the exercise capacity of the user. More specifically, the reliability score is calculated from the measurement results of the heart rate sensor 111 and the acceleration sensor 112. The reliability score is described below more in detail. The reliability score calculator 140 outputs the calculated reliability score to the determiner 150. Based on the reliability score received from the reliability score calculator 140, the determiner 150 determines the reliability of the measurement results of the exercise test. The determiner 150 determines the reliability score, using a specific threshold value. More specifically, the determiner 150 determines whether the reliability score is equal to or higher than the specific threshold value. The determination process of the determiner 150 is described below in detail. The determiner 150 outputs the determination results to the maximum oxygen intake amount estimator 160.

The maximum oxygen intake amount estimator 160 estimates a maximum oxygen intake amount of the user during the exercise test, using the determination results from the determiner 150 and the measurement results from the heart rate sensor 111 and the acceleration sensor 112. The estimation process of the maximum oxygen intake amount estimator 160 is described below in detail. The maximum oxygen intake amount estimator 160 outputs the estimation results to the outputter 170.

Memory

The memory 130 is designed such that a variety of information may be stored thereon and stored information is retrieved therefrom. The memory 130 may a hard disk or a semiconductor memory. The memory 130 stores the maximum acceleration value acquired by the maximum acceleration acquirer 120, and other data.

Outputter

The outputter 170 outputs visually and/or audibly a variety of information input from the exercise test evaluation apparatus 300. For example, the outputter 170 may be a liquid-crystal panel, a display including an organic or inorganic electroluminescence (EL) display panel, or a speaker, or a combination thereof. The outputter 170 may be part of the computer that includes the exercise test evaluation apparatus 300, or part of the computer that does not include the exercise test evaluation apparatus 300, or may be a standalone device. The outputter 170 may be part of the user's terminal, such as a smart phone, a smart watch, or a tablet. The outputter 170 may be mounted together with the sensors 110 on the band 110a of FIG. 2. The outputter 170 outputs the reliability score calculated by the processor 200, and information, such as the maximum oxygen intake amount estimated by the maximum oxygen intake amount estimator 160.

1.2 Process of Exercise Test Evaluation System of the First Embodiment

Figure 4:
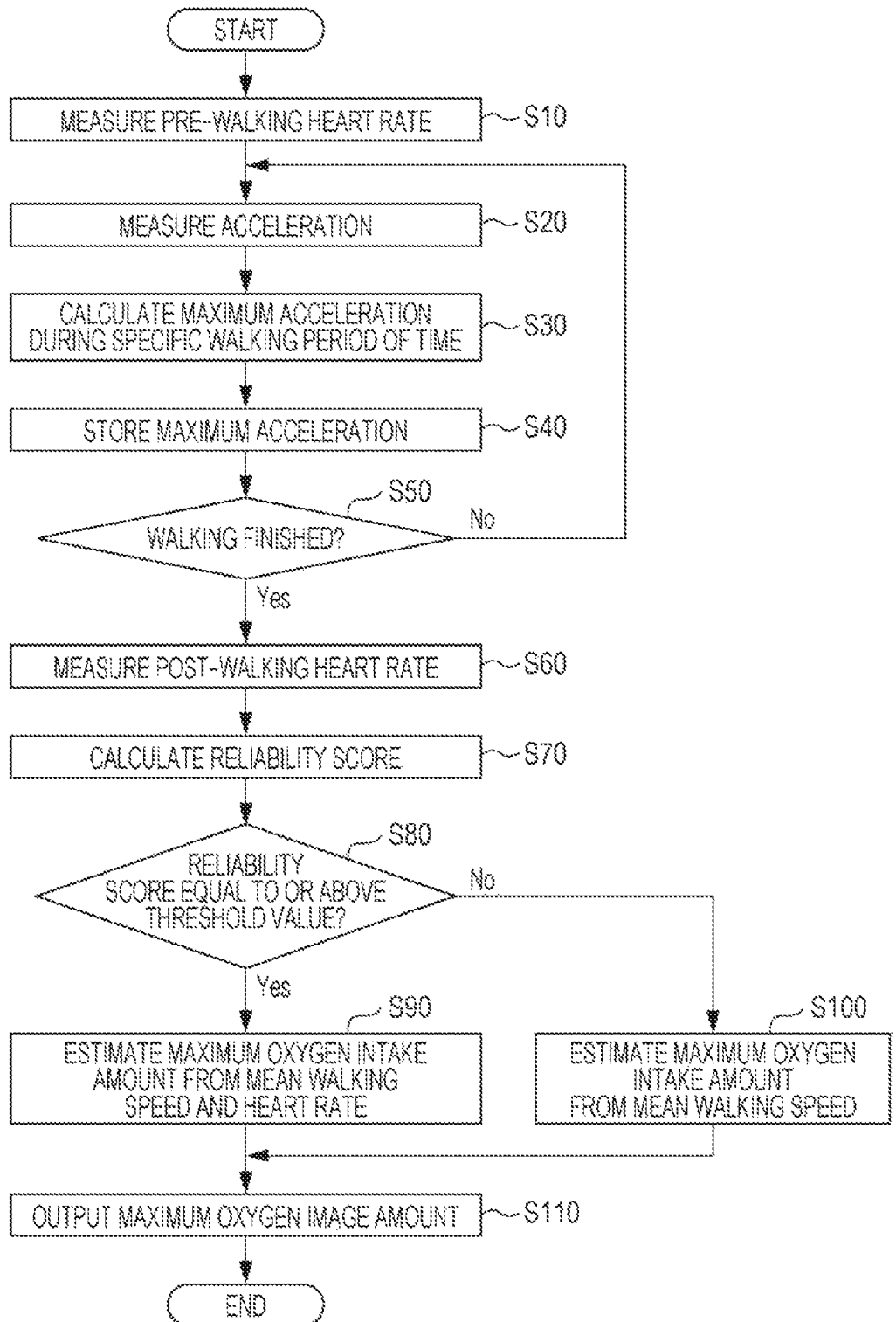
FIG. 4 is a flowchart illustrating an example of a process of an exercise test evaluation system of the first embodiment.

The process of the exercise test evaluation system 100 of the first embodiment is described with reference to FIG. 4. FIG. 4 is a flowchart illustrating a process of the exercise test evaluation system 100 of the first embodiment. In accordance with the first embodiment, the user performs a 6-minute walk test (6MWT) as the exercise test.

Step S10

Before the user starts walking, the exercise test evaluation system 100 measures the heart rate of the user at rest by operating the heart rate sensor 111. For example, the exercise test evaluation system 100 measures the heart rate of the user at rest with the heart rate sensor 111 before the user starts walking. For example, the exercise test evaluation system 100 requests the user to be at rest using the outputter 170 and then measures the heart rate of the user with the heart rate sensor 111. The heart rate sensor 111 outputs the measurement results of heart rate to the maximum oxygen intake amount estimator 160. Alternatively, the heart rate sensor 111 may output the measurement results to the memory 130 for storage. The heart rate sensor 111 may output the measurement results to both the maximum oxygen intake amount estimator 160 and the memory 130. The heart rate sensor 111 may output the heart rate measurement results together with measurement time. Alternatively, the exercise test evaluation apparatus 300 may associate the heart rate measurement results acquired from the heart rate sensor 111 with the measurement time. In accordance with the first embodiment, the exercise test evaluation system 100 causes the heart rate sensor 111 to stop operating after the heart rate measurement prior to the start of the exercise test. Alternatively, the exercise test evaluation system 100 may cause the heart rate sensor 111 to continuously operate to measure the heart rate until the exercise test is complete.

Step S20

Before the user starts walking, the exercise test evaluation system 100 causes the acceleration sensor 112 to operate to measure acceleration of the foot of the user. During the 6 minute test, the acceleration sensor 112 continuously measures the acceleration of the foot of the user. Although the acceleration sensor 112 outputs acceleration values as the measurement results of acceleration to the maximum acceleration acquirer 120, the acceleration sensor 112 may instead output the acceleration values to the memory 130 for storage. The acceleration sensor 112 may output the acceleration values to both the maximum acceleration acquirer 120 and the memory 130. The acceleration sensor 112 may also output the acceleration values as the measurement results of acceleration together with measurement time. Alternatively, the exercise test evaluation apparatus 300 may associate the acceleration values as the measurement results of acceleration acquired from the acceleration sensor 112 with the measurement time.

Step S30

During the exercise test of the user, in other words, during walking, the maximum acceleration acquirer 120 acquires sequentially in time the acceleration values as the measurement results of acceleration of the user's foot from the acceleration sensor 112. The maximum acceleration acquirer 120 then segments the acceleration values as the measurement results of acceleration of the user's foot according to a specific time period that is a constant time period. The maximum acceleration acquirer 120 then acquires a maximum acceleration value from among the acceleration values of the user's foot within each specific time period. The specific time period may be referred to as a first specific time period. Referring to FIG. 3, for example, the first time period is 6.0 seconds. The maximum acceleration value within the first time period of FIG. 3 is an acceleration value of 25800 mG at a time point of 3.2 seconds.

The maximum acceleration acquirer 120 extracts multiple acceleration values higher than the rest of the acceleration values of acceleration of the user's foot within the first time period, and sets the mean value of the extracted acceleration values to be a maximum acceleration value within the first time period. For example, the multiple acceleration values that are higher than the other acceleration values may include the highest acceleration value, the second highest acceleration value, and the third highest acceleration value.

The maximum acceleration acquirer 120 may detect a gait cycle of the user from the acquired acceleration, calculate a maximum value of acceleration from acceleration values within each gait cycle, calculate a mean value of the maximum acceleration values of at least one gait cycle, and use the calculated mean value as a maximum acceleration value. For example, the maximum acceleration acquirer 120 extracts a maximum value of acceleration from each of groups adjacent to each other with each group including acceleration values equal to or higher than a specific value in a waveform of the acquired acceleration, and acquires as a gait cycle a time period between the two maximum acceleration values of the adjacent groups. For example, the gait cycle is a time period between two adjacent peaks or two adjacent troughs in the waveform of acceleration illustrated in FIG. 3. In this way, the maximum acceleration acquirer 120 may acquire a maximum value of acceleration on each gait cycle.

Step S40

The maximum acceleration acquirer 120 associates the acquired maximum acceleration value with the measurement time at which the maximum acceleration value is acquired, and then stores the maximum acceleration value and the measurement time in association with each other on the memory 130. The time measurement may be performed with respect to time set up within the first time period that is unit time. Alternatively, the time measurement may be performed with respect to time set up regardless of the first time period. For example, the time measurement is performed, starting at time set up as a reference at the start time of the exercise test. The time measurement based on time set up regardless of the first time period may be represented by a time point when a maximum acceleration value is measured. For example, if the mean value of multiple higher acceleration values is set up as a maximum acceleration value, the mean value of time periods within which the maximum acceleration values are measured is associated with the maximum acceleration value.

The maximum acceleration acquirer 120 may acquire from the sensors 110 data that associates a measurement value of acceleration with measurement time. Alternatively, the maximum acceleration acquirer 120 may sequentially acquire acceleration values in the order of measurement from the acceleration sensor 112 and may acquire time at which each acceleration value is measured, by referencing information of a measurement period of the acceleration sensor 112.

FIG. 5 illustrates an example of data to be stored on the memory 130. Each piece of the data is tagged with a time sequence number in the order of storage. Each piece of the data includes the time sequence number, a time segment corresponding to the time sequence number, and a maximum acceleration value extracted from acceleration values within the time segment. The range of time of the time segment is defined by time. The data of FIG. 5 lists a maximum acceleration value within 1 minute when the first time period serving a specific time period is 1 minute. In this way, the maximum acceleration acquirer 120 acquires a maximum acceleration value per specific time period, and stores the maximum acceleration value onto the memory 130.

Step S50

By referencing elapsed time, the maximum acceleration acquirer 120 determines whether the exercise test, namely, walking has been completed. If the acceleration sensor 112 fails to detect an acceleration value equal to or higher than a specific value within the specific time period, the maximum acceleration acquirer 120 determines that the exercise test has been completed. For example, the specific value may be an acceleration value when the user does not perform the exercise test. If the maximum acceleration acquirer 120 acquires, from information input from an external device, information indicating the end of the exercise test, the maximum acceleration acquirer 120 may determine that the exercise test has been completed. If the exercise test is in progress (no branch from step S50), the maximum acceleration acquirer 120 returns to the operation in step S20. If the exercise test has been completed (yes branch from step S50), the maximum acceleration acquirer 120 proceeds to an operation in step S60.

Step S60

After the exercise test, the exercise test evaluation system 100 causes the heart rate sensor 111 to operate to measure the heart rate of the user who has completed the exercise test. The processor 200 sends to the heart rate sensor 111 end information including time at which the exercise test is complete. In response to the end information, the heart rate sensor 111 starts measuring the heart rate. For example, the heart rate sensor 111 starts measuring the heart rate within 30 seconds from the time when the exercise test has been completed. If the heart rate sensor 111 continues to measure the heart rate after the beginning of the exercise test, the exercise test evaluation system 100 may cause the heart rate sensor 111 to continue to measure the heart rate after the end of the exercise test.

Step S70

The reliability score calculator 140 calculates the reliability score that corresponds to a change in the maximum acceleration value with time. The reliability score calculator 140 acquires from the memory 130 a maximum acceleration values associated with measurement time as listed in FIG. 5. The maximum acceleration value acquired is a maximum acceleration value that is calculated from the acceleration values as the measurement results obtained during the whole time period of the exercise test. Using the maximum acceleration value acquired, the reliability score calculator 140 calculates the reliability score corresponding to a change in the maximum acceleration value with time. For example, the reliability score calculator 140 calculates the reliability score from the maximum acceleration value and the time sequence number corresponding to the maximum acceleration value. More specifically, the reliability score is calculated in accordance with the following formula:

Reliability score=(Time sequence number having the lowest maximum acceleration value)−(Time sequence number having the highest maximum acceleration value)

In the example of FIG. 5, the time sequence number having the lowest maximum acceleration value is 5 (corresponding to time segment of 4 to 5 minutes), and the time sequence number having the highest maximum acceleration value is 2 (corresponding to time segment of 1 to 2 minutes). The reliability score is thus 3.

The maximum acceleration value in the moving direction represents a strength with which the user takes a step forward, and becomes lower as the degree of fatigue of the user increases. The reliability score calculated in accordance with the above formula is an index that represents the effort made by the user during the exercise test. For example, if the user tries to walk as fast as he or she can from the start of walking, the user may be gradually tired, and the reliability score becomes larger in positive value. Conversely, if the user tries to walk fast for some last moments, the reliability score becomes a negative value. In the latter case, the user has still enough energy left and the reliability of the entire exercise test is considered to be low. In accordance with the first embodiment, the reliability of the entire exercise test is considered to be higher as the reliability score is higher.

Step S80

The determiner 150 receives the reliability score from the reliability score calculator 140, and determines whether the acquired reliability score is equal to or higher than a first specific threshold value. An example of the first specific threshold value is 0. If the reliability score is 0, the user seems to try to walk with a certain degree of effort to keep his or her own pace throughout the exercise test. The reliability of the whole exercise test is considered to be higher. If the reliability score is higher than 0, the user seems to make too much effort to raise the walking velocity during the first half portion of the exercise test, and the reliability of the whole exercise test is considered to be higher. If the reliability score is lower than 0, the reliability of the whole exercise test is considered to be lower as described above. If the reliability score is equal to or higher than the first specific threshold value (yes branch from step S80), the determiner 150 proceeds to an operation in step S90. If the reliability score is lower than the first specific threshold value (no branch from step S80), the determiner 150 proceeds to an operation in step S100. The first specific threshold value related to the reliability score may be a value according to which the reliability of the whole exercise test is determined to be higher. In view of this, the specific threshold value related to the reliability score may be a value higher than 0.

Step S90

If the reliability score is equal to or higher than the first specific threshold value, the maximum oxygen intake amount estimator 160 acquires the measurement results of the heart rate from the heart rate sensor 111, and the measurement results of acceleration from the acceleration sensor 112. The maximum oxygen intake amount estimator 160 calculates the mean walking velocity of the user from the acceleration values as the measurement results of the acquired acceleration values. The maximum oxygen intake amount estimator 160 further estimates the maximum oxygen intake amount in response to first criteria, the mean walking velocity, and the heart rate of the user. The mean walking velocity is the mean walking velocity of the user during the exercise test. The first criteria may be indicated in a formula or table that associates the mean walking velocity, the heart rate, and the maximum oxygen intake amount. In this way, the first criteria may serve as criteria that associate the mean walking velocity and heart rate with the maximum oxygen intake amount.

The maximum oxygen intake amount estimator 160 may integrate the acceleration value acquired from the acceleration sensor 112 with time during the exercise test, and calculate the mean walking velocity using the integration value. Also, the maximum oxygen intake amount estimator 160 may calculate the mean walking velocity using a travel distance of the user during the exercise test, and a time period of the exercise test throughout which the exercise test is performed. The maximum oxygen intake amount estimator 160 may acquire the heart rate after the exercise test measured in step S60, as information of the heart rate. The maximum oxygen intake amount estimator 160 may acquire a change between the heart rate before the exercise test measured in step S10 and the heart rate after the exercise test. The maximum oxygen intake amount estimator 160 may estimate the maximum oxygen intake amount in accordance with the linear regression or logistic regression using the mean walking velocity and the heart rate. In the case of linear regression, let Y, X1, and X2 represent the maximum oxygen intake amount, the mean walking velocity and the heart rate, respectively, and the maximum oxygen intake amount is predicted in accordance with formula Y=X0+ X1·W1+X2·W2. Parameters X0, W1, and W2 used in this prediction are calculated from learning data in advance. The learning data may be measurement data that is obtained by measuring a set of the maximum oxygen intake amount, the mean walking velocity, and the heart rate on multiple subjects.

Step S100

If the reliability score is lower than the first specific threshold value, the maximum oxygen intake amount estimator 160 acquires the mean walking velocity in a similar way as in the operation in step S90. The maximum oxygen intake amount estimator 160 estimates the maximum oxygen intake amount in response to second criteria and the mean walking velocity. The second criteria may be indicated in a formula or table that associates the mean walking velocity with the maximum oxygen intake amount. In this way, the second criteria may serve as criteria that associate the mean walking velocity with the maximum oxygen intake amount. The maximum oxygen intake amount estimator 160 may estimate the maximum oxygen intake amount in accordance with the linear regression or logistic regression using the mean walking velocity.

The mean walking velocity is separately calculated in step S90 and S100. Alternatively, the mean walking velocity may be calculated between step S70 and step S80, and the calculated mean walking velocity may be referenced in steps S90 and S100. The calculation method of the mean walking velocity may be identical to the calculation method described with reference to step S90.

Step S110

The outputter 170 receives the estimated maximum oxygen intake amount from the maximum oxygen intake amount estimator 160, and outputs the received maximum oxygen intake amount. The processor 200 may output, to an external device, information of the maximum oxygen intake amount estimated by the maximum oxygen intake amount estimator 160. If the determination results in step S80 indicate that the reliability score is lower than the first specific threshold value, the processor 200 may provide to the outputter 170 a recommendation for an exercise retest or an error display indicating that no results are obtained from the exercise test. For example, the results of the exercise test having a low reliability score may possibly suggest an erroneous status of the exercise capacity of the user. The processor 200 may perform a determination as to whether the outputter 170 is provided with the recommendation for the exercise retest or the error display, using a threshold value of another reliability score lower than the first specific threshold value.

The reason why the operations in steps S90 and S100 are performed described below. In accordance with the first embodiment, an experiment was conducted on multiple subjects to estimate the maximum oxygen intake amount from the measurement results. During the experiment, the maximum oxygen intake amount was estimated while the combination of the reliability score and the estimation method of the maximum oxygen intake amount was changed. The subjects participated in the experiment were 24 aged persons. Each subject underwent the 6-minute walk test and a cardio-pulmonary exercise test. The cardio-pulmonary exercise test measures a maximum oxygen intake amount that serves as an accurate index of endurance. FIG. 6A, FIG. 6B, FIG. 7A and FIG. 7B illustrate estimation results of the maximum oxygen intake amount in each combination of the reliability score and the estimation method of the maximum oxygen intake amount. As described below, FIG. 6A, FIG. 6B, FIG. 7A and FIG. 7B indicate a difference in the estimation accuracy of the maximum oxygen intake amount.

Figure 6A:
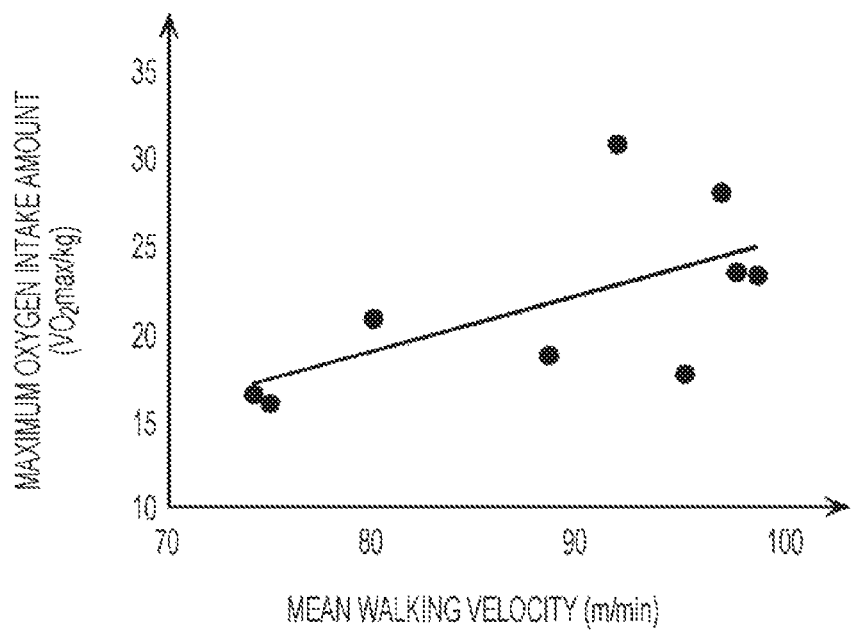
FIG. 6A illustrates an example of a correlation between a mean walking velocity and a maximum oxygen intake amount during a 6-minute walk test.
Figure 6B:
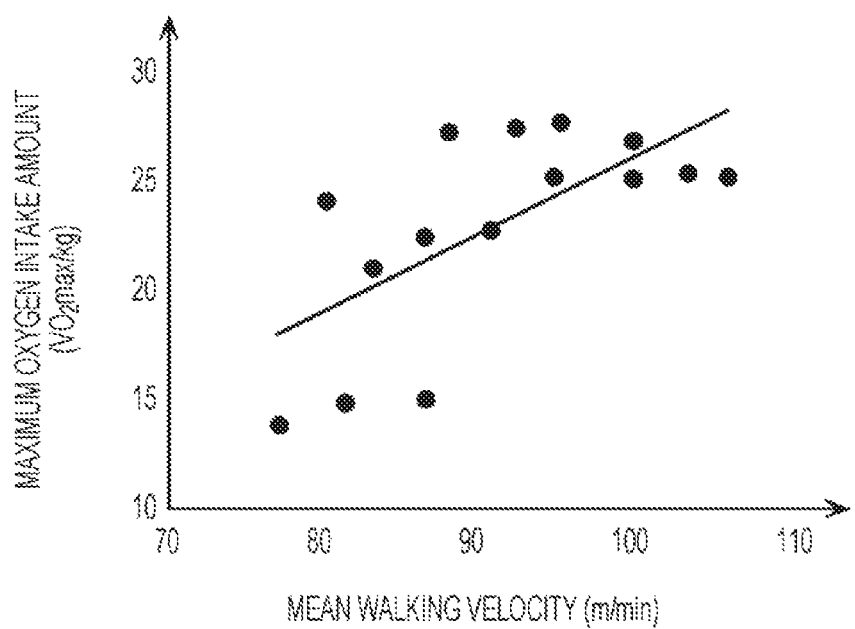
FIG. 6B illustrates another example of the correlation between the mean walking velocity and the maximum oxygen intake amount during the 6-minute walk test.
Figure 7A:
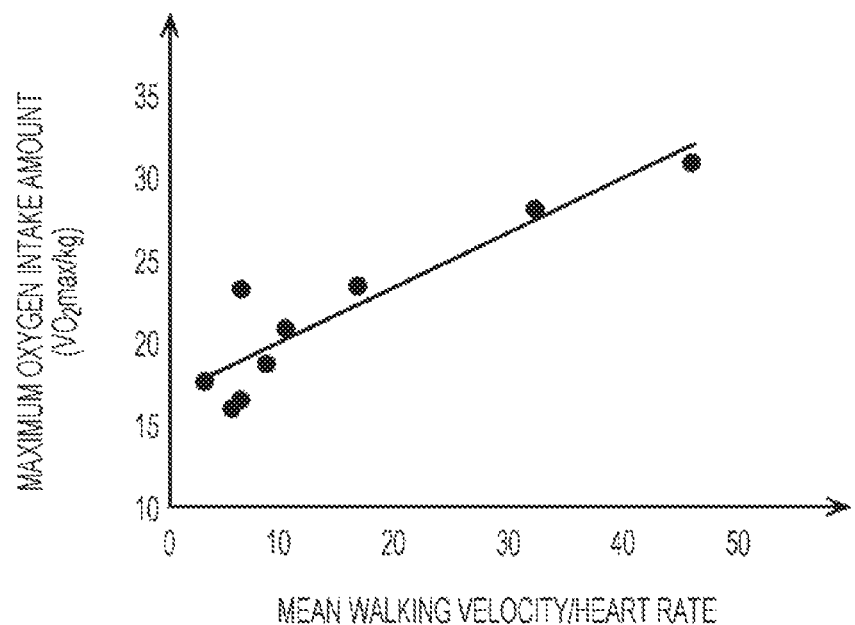
FIG. 7A illustrates an example of a correlation between the mean walking velocity/heart rate and the maximum oxygen intake amount during the 6-minute walk test.
Figure 7B:
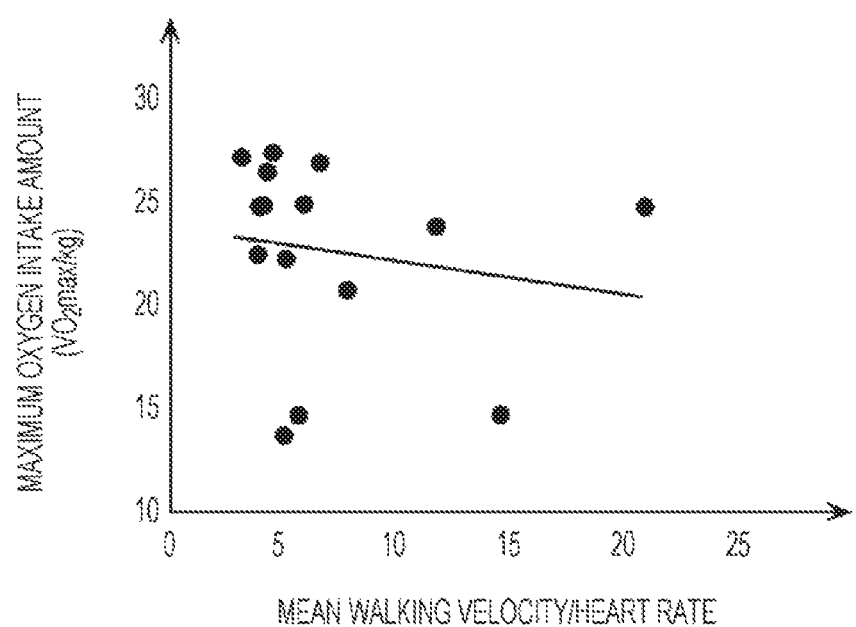
FIG. 7B illustrates another example of the correlation between the mean walking velocity/heart rate and the maximum oxygen intake amount during the 6-minute walk test.

Experiment results of FIG. 6A and FIG. 6B indicate the maximum oxygen intake amounts ($VO_2$ max/kg) that are estimated using an index "mean walking velocity" (m/min) that is calculated in the 6-minute walk test. Experiment results of FIG. 7A and FIG. 7B indicate the maximum oxygen intake amounts ($VO_2$ max/kg) that are estimated using an index of "mean walking velocity/heart rate" that is calculated in the 6-minute walk test. Referring to FIG. 6A and FIG. 6B, the vertical axis represents the maximum oxygen intake amount and the horizontal axis represents the mean walking velocity. Referring to FIG. 7A and FIG. 7B, the vertical axis represents the maximum oxygen intake amount and the horizontal axis represents the mean walking velocity/heart rate.

FIG. 6A and FIG. 7A represent experiment results of subjects who have a positive reliability score, and FIG. 6B and FIG. 7B represent experiment results of subjects who have a negative reliability score. A correlation between the index calculated in the 6-minute walk test and the maximum oxygen intake amount is calculated from the experiment results of each of FIG. 6A and FIG. 7A, and FIG. 6B and FIG. 7B.

More specifically, the experiment results in FIG. 6A and FIG. 7A indicate that the maximum oxygen intake amount is estimated at a high degree of accuracy in the experiments of the subjects having a positive reliability score using the index of "mean walking velocity/heart rate". With respect to a linear relationship between the variable "mean walking velocity" or "mean walking velocity/heart rate" and the variable "maximum oxygen intake amount", a correlation coefficient R of 0.61 is obtained from FIG. 6A and a correlation coefficient R of 0.91 is obtained from FIG. 7A. The correlation coefficient refers to the gradient of the line segment illustrated in FIG. 6A and FIG. 7A. Therefore, the correlation between the variable "mean walking velocity/heart rate" and the variable "maximum oxygen intake amount" illustrated in FIG. 7A is higher than the correlation between the variable "mean walking velocity" and the variable "maximum oxygen intake amount" illustrated in FIG. 6A.

In the experiment results of the subjects having a negative reliability score as illustrated in FIG. 6B and FIG. 7B, a correlation coefficient R of 0.65 is obtained from FIG. 6B and a correlation coefficient R of −0.16 is obtained from FIG. 7B. The correlation coefficient refers to the gradient of the line segment illustrated in FIG. 6B and FIG. 7B. The correlation between the variable "mean walking velocity" and the variable "maximum oxygen intake amount" illustrated in FIG. 6B is thus higher than the correlation between the variable "mean walking velocity/heart rate" and the variable "maximum oxygen intake amount" illustrated in FIG. 7B.

The reliability score represents the degree of effort the subject makes in walking, and is thus affected by the reliability of the heart rate in terms of variation. The experiment results indicate that in an effective estimation method of the maximum oxygen intake amount, the heart rate is used if the reliability score is positive and the heart rate is not used if the reliability score is negative.

By comparing FIG. 7A and FIG. 7B corresponding to maximum and minimum correlation coefficients, a relationship between the reliability score and the estimation accuracy of the maximum oxygen intake amount is examined. From the experiment results, the correlation coefficient is 0.91 in FIG. 7A where the reliability score of each subject is positive, and the correlation coefficient is negative and as low as −0.16 in FIG. 7B where the reliability score of each subject is negative. It is thus recognized in FIG. 7A that the maximum oxygen intake amount is estimated at a high degree of accuracy from the walking velocity and heart rate measured in the 6-minute walk test. The experiment results indicate that the reliability score is proved useful as an index that quantitatively evaluates the reliability of the exercise test.

As described above, the exercise test evaluation system 100 of the first embodiment numerically evaluates the reliability of the measurement results of the exercise test using the reliability score, and estimates the maximum oxygen intake amount of a subject at a high degree of accuracy in the exercise test. The reliability score is acquired in accordance with the maximum acceleration value of the foot during each of the multiple time periods. A variation pattern of the maximum acceleration value of the foot during the exercise test may be displayed. If the reliability score is equal to or higher than the first specific threshold value, the maximum oxygen intake amount may be estimated using the user's walking velocity and heart rate during the exercise test. If the reliability score is lower than the first specific threshold value, the maximum oxygen intake amount may be estimated using the user's walking velocity during the exercise test rather than using the user's heart rate that affects the reliability score. The maximum oxygen intake amount of the subject is thus estimated at a high degree of accuracy.

Second Embodiment

The exercise test evaluation system 100 of the first embodiment estimates the maximum oxygen intake amount of the subject, by evaluating the measurement results of the exercise test using the reliability score. In contrast, an exercise test evaluation system 100A of a second embodiment outputs estimation results of the exercise capacity of a subject, such as endurance of the subject, based on the reliability score. The following discussion focuses on a difference between the first embodiment and the second embodiment. In the discussion of the second embodiment, elements identical to those of the first embodiment are designated with the same reference numerals.

Figure 8:
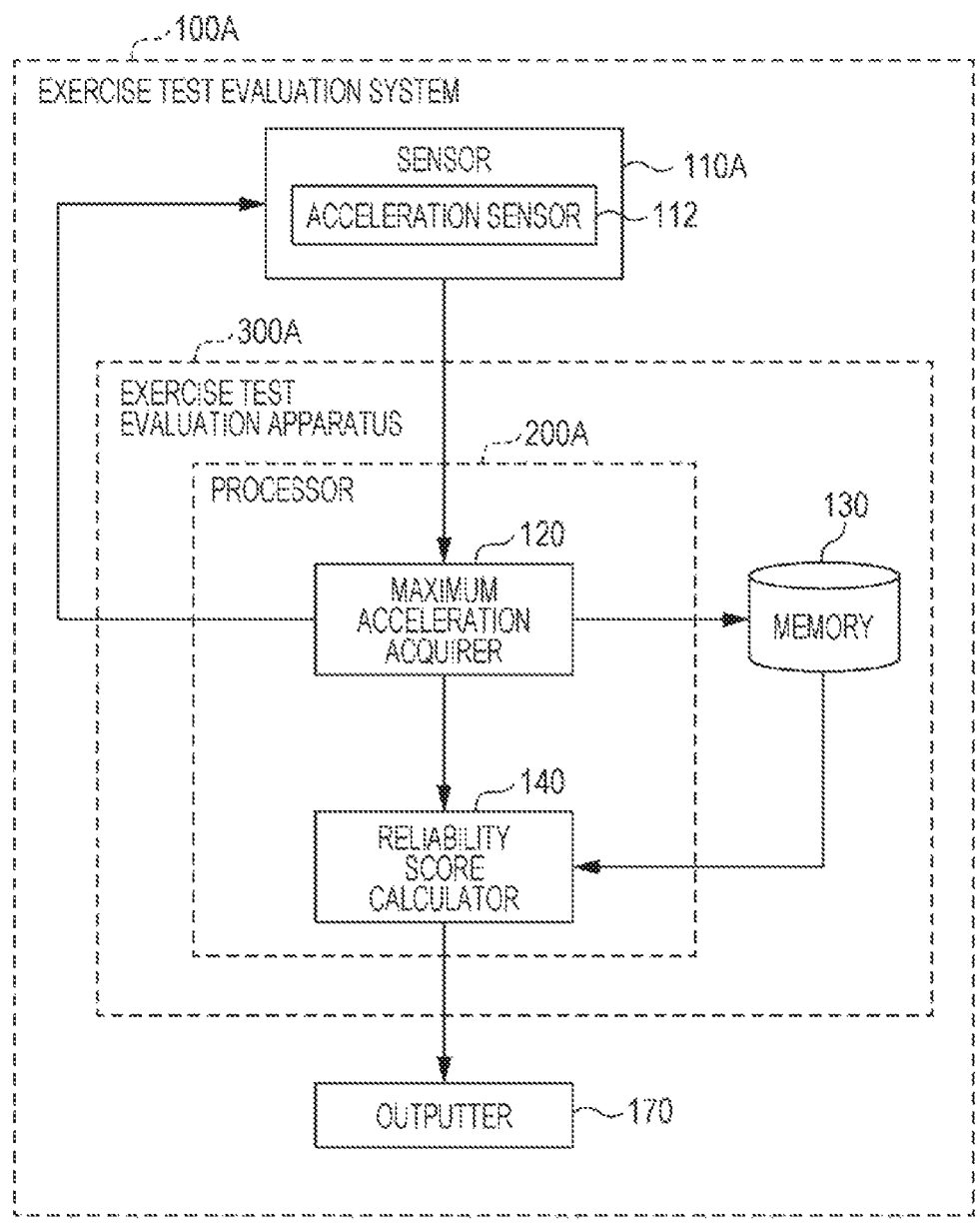
FIG. 8 is a block diagram illustrating an exercise test evaluation system of a second embodiment.

FIG. 8 is a block diagram illustrating the configuration of the exercise test evaluation system 100A of the second embodiment. Referring to FIG. 8, the difference in configuration between the exercise test evaluation system 100A of the second embodiment and the exercise test evaluation system 100 of the first embodiment is that the exercise test evaluation system 100A is without the determiner 150 and the maximum oxygen intake amount estimator 160. The exercise test evaluation system 100A further includes an acceleration sensor 110a, an outputter 170A, and an exercise test evaluation apparatus 300A. The acceleration sensor 110a includes the acceleration sensor 112 but does not include the heart rate sensor 111. In the exercise test evaluation system 100A, the processor 200A includes the maximum acceleration acquirer 120 and the reliability score calculator 140. The processor 200A calculates the reliability score of the exercise test, based on an acceleration value detected by the acceleration sensor 110a. The exercise test evaluation apparatus 300A further includes the processor 200A and the memory 130. The rest of the exercise test evaluation system 100A is identical in configuration to the exercise test evaluation system 100 of the first embodiment and the discussion thereof is omitted herein.

Figure 9:
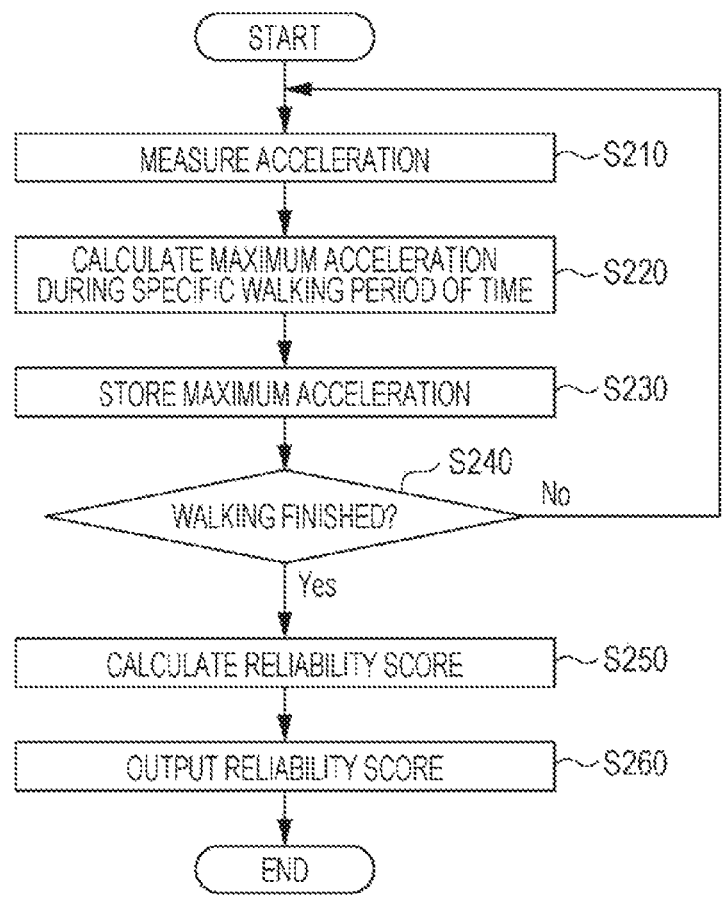
FIG. 9 is a flowchart illustrating an example of a process of the exercise test evaluation system of the second embodiment.

Referring to FIG. 9, the process of the exercise test evaluation system 100A of the second embodiment is described below. FIG. 9 is a flowchart illustrating the process of the exercise test evaluation system 100A of the second embodiment. In the second embodiment as well, the 6-minute walk test is used as an exercise test.

Steps S210 through S230

Operations in steps S210 through S230 to be performed by the exercise test evaluation system 100A are respectively identical to the operations in steps S20 through S40 performed by the exercise test evaluation system 100 of the first embodiment.

Step S240

The maximum acceleration acquirer 120 determines whether the exercise test, namely, walking has been completed. If the exercise test still continues (no branch from step S240), the maximum acceleration acquirer 120 returns to the operation in step S210. If the exercise test has been completed (yes branch from step S240), the maximum acceleration acquirer 120 proceeds to step S250.

Step S250

The reliability score calculator 140 calculates the reliability score by retrieving from the memory 130 the maximum acceleration value associated with the measurement time as illustrated in FIG. 5. The maximum acceleration value acquired is a maximum acceleration value that has been calculated from the measurement results over the whole period of the exercise test. For example, the reliability score calculator 140 calculates the reliability score from the measurement time and the maximum acceleration value stored on the memory 130. The calculation method of the reliability score is identical to the calculation method of the first embodiment.

Step S260

The processor 200A causes the outputter 170 to output the reliability score calculated in step S250. If the reliability score is equal to or higher than a second specific threshold value, the processor 200A may output an endurance evaluation value by the exercise test to the outputter 170 or an external device. The endurance evaluation value by the exercise test may be obtained through a method adopted in the 6-minute walk test. If the reliability score is lower the second specific threshold value, the processor 200A may cause the outputter 170 to output an indication that the exercise test is repeated or that the endurance evaluation value by the exercise test is not output. The processor 200A may output the reliability score to the external device. The processor 200A may further output information as to the maximum oxygen intake amount of the subject. The second specific threshold value of the reliability score may or may not be equal to the first specific threshold value of the reliability score of the first embodiment.

The reliability of the exercise test may be evaluated through the operations in steps S210 through S260. The reliability of the exercise test may be quantitatively evaluated using the reliability score. The endurance of the subject is accurately estimated by repeating the exercise test if the reliability score is lower.

As described above, the exercise test evaluation system 100A of the second embodiment may numerically output the reliability of the measurement results of the exercise test using the reliability score. The reliability score may be acquired in accordance with the maximum acceleration value of the foot in each of the time periods, and may indicate a variation pattern of the maximum acceleration value of the foot during the exercise test. In this way, the user of the exercise test evaluation system 100A may numerically determine the reliability of the results of the exercise test, such as the endurance of the user, in accordance with the reliability score. The exercise test evaluation system 100A may also determine the reliability. Based on the determination results, the exercise test evaluation system 100A may display an error in the results of the exercise test or recommend the repetition of the exercise test. In this way, the exercise test evaluation system 100A increases the estimation accuracy of the exercise capacity of the user, such as endurance of the user.

Modifications of Reliability Score of the First and Second Embodiments

In accordance with the first and second embodiments, the reliability score is calculated in accordance with formula "Reliability score=(Time sequence number having the lowest maximum acceleration value)−(Time sequence number having the highest maximum acceleration value)" using multiple maximum acceleration values and the time sequence numbers thereof. In accordance with a modification of the embodiments, the reliability score calculator 140 re-arranges the multiple maximum acceleration values in the order of larger to smaller magnitude. The reliability score calculator 140 then determines the absolute value of a difference between an order number of each maximum acceleration value indicating the arrangement order of the multiple maximum acceleration values arranged in the order of larger to smaller magnitude and the time sequence number of the corresponding maximum acceleration value. The reliability score calculator 140 sums the absolute values of the differences of all the maximum acceleration values, and thus sets the sum to be the reliability score.

As illustrated in FIG. 5, for example, the maximum acceleration values of the time segments are arranged in the order from larger to smaller magnitude. The order numbers of the maximum acceleration values of the time sequence numbers 1, 2, 3, 4, 5, and 6 are 2, 1, 3, 4, 6, and 5, respectively. In this case, the reliability score is 4. If the degree of effort made by the user during the exercise test is higher, the time sequence number is closer to the order number in each maximum acceleration value. In accordance with the modification, it is recognized that the higher the reliability score is, the lower the reliability is.

The calculation method of the reliability score in the first and second embodiments pays attention to the two maximum acceleration values when the maximum acceleration value that is minimum and the maximum acceleration value that is maximum are attained in time. The calculation method of the reliability score in accordance with the modification calculates the reliability score using all the maximum acceleration values throughout the exercise test. The reliability score is thus calculated, focusing on and reflecting the walking pattern of the user throughout the exercise test. The reliability score calculated in the modification reflects the walking status of the user at a higher degree of accuracy.

Other Modifications

The exercise test evaluation systems of one or more aspects have been described in accordance with the embodiments and the modification thereof. The disclosure is not limited to the embodiments and modification. A variety of modifications apparent to those skilled in the art may be applied to the embodiments and modification to form a new embodiment or elements in the different embodiments may be combined to form a new embodiment. Those new embodiments may fall within the scope of the one or more aspect of the disclosure as long as they do not depart from the spirit of the disclosure.

In accordance with the embodiments and modification, the exercise test evaluation system estimates the exercise capacity of the walking of the user in response to the value detected by the acceleration sensor 112 that is worn by the foot of the user. The disclosure is not limited to this arrangement. The acceleration sensor 112 may be attached to any part of the user's body, including an arm or another part. The exercise test evaluation system may estimate the exercise capacity related to a moving part of the body.

In accordance with the disclosure, all or some of the units, apparatuses, members, and modules or some or all of functional blocks described with reference to FIG. 1 through FIG. 8 are implemented by one or more electronic circuits. The electronic circuit may include a semiconductor device, a semiconductor integrated circuit (IC), or a large-scale integrated circuit (LSI). The LSI or IC may be integrated into a single chip or mounted on multiple chips. A functional block, such as a storage unit other than a memory, may be integrated into the single chip. The electronic circuit may also be a system LSI, very large scale integrated circuit (VLSI), or ultra large scale integrated circuit (ULSI), depending, different from each other in the degree of integration.

A field programmable gate array (FPGA) or a reconfigurable logic device (RLD) may be used for the same purpose. The FPGA is programmable after the manufacture of the LSI. The RLD is reconfigurable in terms of the connection in the LSI or allows internal segments to be set up in the LSI.

The function or operation of all or some of the units, apparatuses, members, and modules may be implemented using software. In such a case, the software may be recorded on one of non-transitory recording media, including one or more read-only memories (ROMs), optical disks, and hard disk drives. The function implemented by the software is executed by a processor or a peripheral device thereof. The system or device may include one or more non-transitory recording media, a processor, and a hardware device, such as an interface.

The disclosure finds applications in techniques that evaluate reliability of an exercise test for a subject.

What is claimed is:

1. An evaluation system, comprising:
    an acceleration sensor that is worn by a user and measures acceleration values of a foot of the user during periods of a walking activity, the periods being a sum of a first period through an n-th period, n being a natural number equal to two or more, an (i+1th) period being provided immediately after the i-th period in a time axis, i being a natural number and (i+1) being equal to n or lower;
    a heart rate sensor that is worn by the user and measures a heart rate of the user after the walking activity;
    a processor that is configured to
        determine a maximum acceleration value for each of the periods to obtain maximum acceleration values corresponding to the periods,
        select a maximum value and a minimum value from among the maximum acceleration values,
        when the maximum value corresponds to a j-th period and the minimum value corresponds to a k-th period, calculate (k−j) as a reliability score, k being a natural number equal to or lower than n, j being a natural number equal to or lower than n, and k not being equal to j,
        when the reliability score is equal to or higher than a specific threshold value, estimate a first maximum oxygen intake amount using both a walking velocity of the user during the walking activity and the heart rate of the user after the walking activity, and
        when the reliability score is lower than the specific threshold value, estimate a second maximum oxygen intake amount using the walking velocity of the user without using the heart rate of the user after the walking activity; and
    an outputter that outputs the first maximum oxygen intake amount or the second maximum oxygen intake amount.

2. The evaluation system according to claim 1, wherein the processor (i) determines a gait cycle of the user on the basis of the acceleration values, and (ii) determines the j-th period and the k-th period on the basis of the gait cycle.

3. An evaluation apparatus, comprising:
    a processor,
    wherein the processor acquires acceleration values of a foot of the user measured during periods of a walking activity, the periods being a sum of a first period through an n-th period, n being a natural number equal to two or more, an (i+1th) period being provided immediately after the i-th period in a time axis, i being a natural number and (i+1) being equal to n or lower,
    wherein the processor is configured to
        determine a maximum acceleration value for each of the periods to obtain maximum acceleration values corresponding to the periods,
        select a maximum value and a minimum value from among the maximum acceleration values,
        when the maximum value corresponds to a j-th period and the minimum value corresponds to a k-th period, calculate (k−j) as a reliability score, k being a natural number equal to or lower than n, j being a natural number equal to or lower than n, and k not being equal to j,
        when the reliability score is equal to or higher than a specific threshold value, estimate a first maximum oxygen intake amount using both a walking velocity of the user during the walking activity and the heart rate of the user after the walking activity, and
        when the reliability score is lower than the specific threshold value, estimate a second maximum oxygen intake amount using the walking velocity of the user without using the heart rate of the user after the walking activity, and
    wherein the first maximum oxygen intake amount or the second maximum oxygen intake amount is output.

4. A non-transitory computer readable recording medium being non-volatile and storing a control program causing an apparatus including a processor to perform a process, the process comprising:
    acquiring acceleration values of a foot of the user measured during periods of a walking activity, the periods being a sum of a first period through an n-th period, n being a natural number equal to two or more, an (i+1th) period being provided immediately after the i-th period in a time axis, i being a natural number and (i+1) being equal to n or lower;
    determining a maximum acceleration value for each of the periods to obtain maximum acceleration values corresponding to the periods;
    selecting a maximum value and a minimum value from among the maximum acceleration values;
    when the maximum value corresponds to a j-th period and the minimum value corresponds to a k-th period, calculating (k−j) as a reliability score, k being a natural number equal to or lower than n, j being a natural number equal to or lower than n, and k not being equal to j;
    when the reliability score is equal to or higher than a specific threshold value, estimating a first maximum oxygen intake amount using both a walking velocity of the user during the walking activity and the heart rate of the user after the walking activity; and
    when the reliability score is lower than the specific threshold value, estimating a second maximum oxygen intake amount using the walking velocity of the user without using the heart rate of the user after the walking activity,
    wherein the first maximum oxygen intake amount or the second maximum oxygen intake amount is output.

5. The non-transitory computer readable recording medium according to claim 4, wherein the process further comprises:
    determining a gait cycle of the user on the basis of the acceleration values; and determines the j-th period and the k-th period on the basis of the gait cycle.

6. An exercise test evaluation method, comprising:

acquiring acceleration values of a foot of the user measured during periods of a walking activity, the periods being a sum of a first period through an n-th period, n being a natural number equal to two or more, an (i+1)th period being provided immediately after the i-th period in a time axis, i being a natural number and (i+1) being equal to n or lower;

determining a maximum acceleration value for each of the periods to obtain maximum acceleration values corresponding to the periods;

selecting a maximum value and a minimum value from among the maximum acceleration values;

when the maximum value corresponds to a j-th period and the minimum value corresponds to a k-th period, calculating (k−j) as a reliability score, k being a natural number equal to or lower than n, j being a natural number equal to or lower than n, and k not being equal to j;

when the reliability score is equal to or higher than a specific threshold value, estimating a first maximum oxygen intake amount using both a walking velocity of the user during the walking activity and the heart rate of the user after the walking activity; and when the reliability score is lower than the specific threshold value, estimating a second maximum oxygen intake amount using the walking velocity of the user without using the heart rate of the user after the walking activity, wherein the first maximum oxygen intake amount or the second maximum oxygen intake amount is output.

7. An apparatus, comprising:

an acceleration sensor that is worn around a leg of a user and outputs acceleration values during periods of a walking activity, the periods being a sum of first period through an n-th period, n being a natural number equal to two or more, an (i+1)th period being provided immediately after the i-th period in a time axis, i being a natural number and (i+1) being n or lower;

a heart rate sensor that is worn by the user and outputs heart rates;

a processor;

a non-transitory memory that stores in advance information describing a relationship between a mean walking velocity and a maximum oxygen intake amount; and an outputter that outputs a first maximum oxygen intake amount or a second maximum oxygen intake amount, wherein the processor is configured to determine a maximum acceleration value for each of the periods to obtain maximum acceleration values corresponding to the periods, select a maximum value and a minimum value from among the maximum acceleration values, when the maximum value corresponds to a j-th period and the minimum value corresponds to a k-th period, calculate (k−j) as a reliability score, k being a natural number equal to or lower than n, j being a natural number equal to or lower than n, and k not being equal to j, calculate a mean walking velocity during the periods using the acceleration values, when the reliability score is zero or higher, calculate $X0+X1 \cdot W1+X2 \cdot W2$, without referring to the information, as the first maximum oxygen intake amount, X1 being the mean walking velocity, X2 being a heart rate included in the heart rates, the heart rate being measured after the periods, X0, W1, and W2 being constant values, and when the reliability score is lower than zero, determine the second maximum oxygen intake amount by referring to the information without using the acceleration values and the heart rates.

* * * * *